United States Patent [19]

Humes

[11] Patent Number: 5,360,790
[45] Date of Patent: Nov. 1, 1994

[54] METHOD AND FORMULATIONS FOR THE THERAPY OF ACUTE RENAL FAILURE

[75] Inventor: H. David Humes, Ann Arbor, Mich.

[73] Assignee: The Regents of the University of Michigan, Ann Arbor, Mich.

[21] Appl. No.: 110,768

[22] Filed: Aug. 23, 1993

Related U.S. Application Data

[63] Continuation of Ser. No. 978,075, Nov. 18, 1992, abandoned, which is a continuation of Ser. No. 625,411, Dec. 11, 1990, abandoned.

[51] Int. Cl.$^5$ .............................................. A61K 37/36
[52] U.S. Cl. ......................................... 514/12; 514/21
[58] Field of Search ................................... 514/12, 21

[56] References Cited

U.S. PATENT DOCUMENTS

| | | | |
|---|---|---|---|
| 3,917,824 | 11/1975 | Camble et al. | 514/12 |
| 3,948,875 | 4/1976 | Cohen et al. | 514/12 |
| 4,528,186 | 7/1985 | Nishimura et al. | 514/2 |
| 4,717,717 | 1/1988 | Finkenaur | 514/21 |
| 4,742,003 | 5/1988 | Derynck et al. | 530/324 |
| 4,749,683 | 6/1988 | Murphy et al. | 514/2 |
| 4,874,746 | 10/1989 | Antoniades et al. | 514/21 |
| 4,929,442 | 5/1990 | Powell | 424/85.2 |
| 4,944,948 | 7/1990 | Uster et al. | 424/450 |
| 4,959,353 | 9/1990 | Brown et al. | 514/12 |
| 4,968,673 | 11/1990 | Humphrey | 514/58 |

OTHER PUBLICATIONS

Humes et al., The Journal of Clinical Investigation, Inc., (Dec. 1989) 84:1757–1761.
Coimbra et al., American Physiological Society, (1990) pp. F438–F443.
Reiss et al., Abstract (1989) Convention of Am. Society of Nephrology.
Coimbra et al., Abstract (1989) Convention of Am. Society of Nephrology.
Coimbra et al., Abstract (Not yet dated).
Tsau et al., Abstracts (1989) Kidney Int. 35:420.

*Primary Examiner*—Howard E. Schain
*Attorney, Agent, or Firm*—Oblon, Spivak, McClelland, Maier & Neustadt

[57] ABSTRACT

The therapy of patients with nephrotoxic or ischemic acute renal failure with epidermal growth factor and/or transforming growth factor-α is disclosed.

12 Claims, 2 Drawing Sheets

METHOD AND FORMULATIONS FOR THE THERAPY OF ACUTE RENAL FAILURE

This invention was made with government support under Grant No. RO1 DK30879-09 awarded by the National Institute of Diabetes and Digestive and Kidney Diseases. The government has certain rights in the invention.

This application is a continuation of application Ser. No. 07/978,075, filed on Nov. 18, 1992, now abandoned, which was a continuation of Ser. No. 07/625,411, filed on Dec. 11, 1990, now abandoned.

BACKGROUND OF THE INVENTION

1. Field of the Invention

This invention relates to phamaceutical compositions containing epidermal growth factor (EGF) and/or transforming growth factor (TGF)-α and to the use of such compositions in treating acute renal failure.

2. Discussion of the Background

Acute renal failure (ARF) is a common clinical syndrome. It is defined as an abrupt decline in renal function. Most clinicians accept the definition of ARF as a rise in serum creatinine of greater than 0.2 to 0.5 mg/dL per day and a rise in blood urea nitrogen (BUN) of greater than 5 to 10 mg/dL per day over several days.

It may occur in a patient with previously normal renal function but may also be superimposed on stable but impaired renal function. The clinical manifestations of this disorder arise from the decline in glomerular filtration rate (GFR) and the inability of the kidney to excrete the toxic metabolic wastes produced by the body. It is recognized clinically by rising levels of blood urea nitrogen (BUN) and serum creatinine concentration and may present dramatically with a patient progressing from normal renal function to symptomatic uremia within a week.

The syndrome of acute renal failure, as it occurs clinically and in animals, results from a complex interplay among cellular, nephronal, and hemodynamic processes. It is now recognized that loss of renal tubular epithelial cell viability results in loss of continuity of the tubular epithelium along the nephron and formation of cellular debris from injured tubule cells in many forms of acute renal failure.

These processes promote derangement in nephronal functions and integrity by producing intratubular obstruction and backleak of glomerular filtrate and results in renal excretory failure. Consequently, the reversibility of acute renal failure depends on renal epithelial cell regeneration to reconstruct normal nephronal architecture, so that normal urine formation can be reestablished.

Several growth factors, including platelet-derived growth factor (PDGF), epidermal growth factor (EGF), transforming growth factors (TGF)-α and TGF-β, are known to be useful in wound healing and repair processes.

Epidermal growth factor is a known composition or compositions that are either isolated from natural sources or are produced using recombinant DNA techniques. The following publications describe epidermal growth factor, its uses and/or processes for isolating it from natural sources or producing it from recombinant DNA techniques: Camble et al., U.S. Pat. No. 3,917,824; Cohen et al., U.S. Pat. No. 3,948,875; Nishimura et al., U.S. Pat. No. 4,528,186; Bell, Published PCT Patent Application WO 85/00369; Urdea et al., Proc. Natl. Acad. Sci. USA, (1983) 80:7461–7465; Hollenburg, "Epidermal Growth Factor-Urogastrone, A Polypeptide Acquiring Hormonal Status" Acad Press, Inc , N.Y. (1979) pp. 90–132; Carpenter, "Epidermal Growth Factor", in Handbook of Experimental Pharmacology, Vol. 57, Beserga, ed.; Lawn et al., Cell (1978) 15:1157–1174; Savage et al., J. Biol. Chem. (1972) 247:7612–7621.EGF is a mitogenic polypeptide which is capable of stimulating the proliferation of keratinocytes and other mammalian epithelial cells in culture.

Transforming growth factor-α is a known composition or compositions that are either isolated from natural sources or are produced using recombinant DNA techniques. The following publications describe transforming growth factor, its uses and/or processes for isolating it from natural sources producing it from recombinant DNA techniques: Derynck et al., U.S. Pat. No. 4,742,003; Delarco et al., Proc. Nat. Acad. Sci. (USA), (1978) 75:4001–4005; Marquardt et al., Science, (1984) 223;1079–1082. TGF-α activates cells via the EGF receptor and is a potent mitogen to a variety of cells, including epithelial cells and hepatocytes.

Current available treatments for acute renal failure are dependent on etiology. The approach to nephrotoxic or post-ischemic acute renal failure is to prevent or ameliorate renal injury during the developing phase of acute renal failure and to treat established disease with supportive care during the maintenance and recovery phases of acute renal failure. There is currently no available treatment to accelerate repair and recovery from acute renal failure once it is established.

The approach to acute renal failure arising from vascular diseases, glomerulonephritis, and tubulointerstitial nephritis is to suppress the degree of injurious inflammatory processes responsible for these diseases. Once again, there is currently no available treatment to enhance the repair of damaged renal tissue from these processes.

The approach to obstructive acute renal failure is primarily directed to the obstructing process. Similar to the other etiologies of acute renal failure, no current treatment regimens are available to speed repair and recovery of injured renal tissues that arise from obstructive damage.

SUMMARY OF THE INVENTION

Accordingly, it is an object of this invention to provide a new treatment to accelerate repair and recovery from acute renal failure, once it is established.

It is another object of this invention to provide a new treatment to enhance the repair of damaged renal tissue.

It is another object of this invention to provide a new treatment regimen to speed repair and recovery of injured renal tissues.

The present invention provides methods and composition which satisfy all of the above objects of this invention, and other objects, as will be apparent from the description of the invention given hereinbelow. It is based on the inventor's discovery that local factors play a significant role in mediating the regeneration process leading to recovery from acute renal failure. This process of regeneration and repair by surviving epithelial cells at the edge of the injury segment is likely dependent on either autocrine or paracrine production of growth-promoting factors.

From this discovery, the inventor has now further found that EGF and/or TGF-α or a physiologically acceptable salt, solvate or complex thereof can be used in the therapy or prophylaxis of certain renal diseases and renal dysfunctions. More particularly, EGF and/or TGF-α or a physiologically acceptable salt, solvate or complex thereof has been found to be useful in the therapy or prophylaxis of any form of acute renal failure, including nephrotoxic and post-ischemic acute renal failure, glomerulonephritis, vascular diseases, tubulo-interstitial diseases, and obstructive processes.

DETAILED DESCRIPTION OF THE PREFERRED EMBODIMENT

Figure 1:
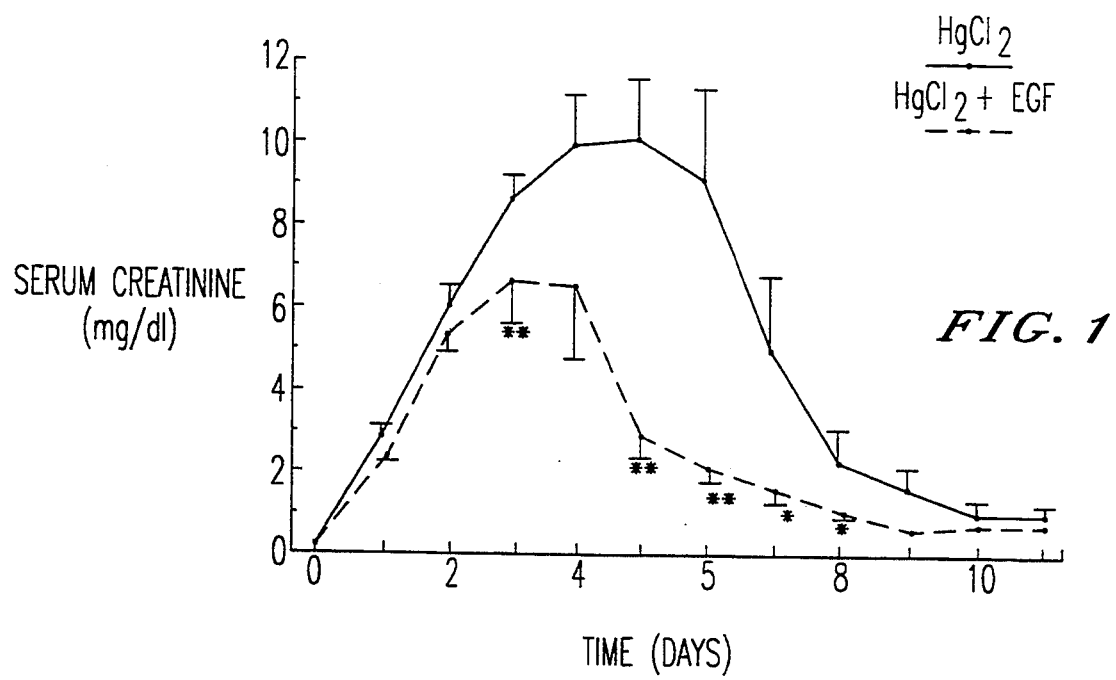
FIGS. 1, 2, 3 and 4 show the effect of EGF in the therapy of acute renal failure.

As used herein, EGF refers both to EGF as described above and to polypeptide products which display biological activity, e.g., mitogenic activity, similar to natural human epidermal growth factor protein as measured in recognized bioassays. As also used herein, TGF-α refers both to TGF-α as described above and to polypeptide products which display biological activity similar to natural human transforming growth factor-α protein as measured in recognized bioassays.

One embodiment of the invention provides a method of treatment of a human or animal subject for combating renal disease by therapy or prophylaxis which method comprises administering to the subject an effective amount of EGF and/or TGF-α or a physiologically acceptable salt, solvate or complex thereof.

In accordance with the invention, both EGF and/or TGF-α can be administered to a patient over a broad range of dosages, utilizing any known route of administration. The range of dosage of administration would vary as a function of the severity of the disease and the patient's condition in a manner known to those of skill in the art, and would fall within the range of from 1 ng $kg^{-1}$ preferably 10 ng $kg^{-1}$, body weight to 10 mg $kg^{-1}$ preferably 1 mg $kg^{-1}$ body weight for both EGF and TGF-α. The active ingredients can be administered by parenteral administration, which includes subcutaneous intramuscular, intraperitoneal, intravenous, and intra-arterial routes.

It is preferable to employ EGF and/or TGF-α or a physiologically acceptable salt, solvate or complex thereof in the form of a formulation. The present invention therefore also provides a composition for use in combating renal disease comprising EGF and/or TGF-α or a physiologically acceptable salt, solvate or complex thereof together, where desirable with one or more carriers or excipients.

The composition may be in a form suitable for oral or parenteral administration or administration through the nasal mucous membranes, for example a snuff. If the composition is for oral administration, for example a tablet or capsule, care should be taken to ensure that the composition enables sufficient active ingredient to be absorbed by the host to produce an effective response. Thus, for example, the amount of active ingredient may be increased over that theoretically required or other known measures such as coating or encapsulation, may be taken to protect the polypeptides from enzymatic action in the stomach.

The pharmaceutical compositions containing the active ingredient in accordance with the invention may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation.

Tablets containing the active ingredient in admixture with non-toxic pharmaceutically acceptable excipients which are suitable for manufacture of tablets may be used. These excipients may be, for example, inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid or talc.

The tablets may be uncoated or they may be coated with known techniques to delay disintegration and absorption in the gastrointestinal track and thereby provide a sustained action over longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example, calcium carbonate, calcium phosphate, or kaolin or as soft gelatin capsules wherein the active ingredient is mixed with water or an oil medium, for example, arachis oil, peanut oil, liquid paraffin or olive oil.

Aqueous suspensions may contain the active materials in the admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecylethyloxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives for example, ethyl or n-propyl p-hydroxybenzoate, one or more coloring agents, one or more flavoring agents and one or more sweetening agents such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oil suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient and admixture with dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oil phase may be a vegetable oil, for example, olive oil or arachis oil, or a mineral oil for example, gum acacia or gum tragacanth, naturally-occurring phosphotides, for example soybean lecithin, and esters or partial esters derived from fatty acids and hexitol anhydrides, for example, sorbitan monooleate, and condensation products of the same partial esters with ethylene oxide, for example, polyoxyethylene sorbitan monooleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectable preparation, for example, as a sterile injectable aqueous or oleaginous suspension. This suspension may be formulated according to the known art using those suitable dispersing or wetting agents and suspending agents which have been mentioned above. The sterile injectable preparations may also be a sterile injectable solution or suspension in a non-toxic parenterally-acceptable diluent or solvate, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this period any bland fixed oil may be employed including synthetic mono- or diglycerides. In addition, fatty acids such as oleic acid find use in the preparation of injectables.

However, preferred composition are those suitable for parenteral administration, i.e., by injection or infusion, and such compositions must be sterile and pyrogen free. Examples of such suitable compositions are sterile injectable solutions or suspensions, and sterile injectable depot or slow-release formulations. An injectable solution or suspension from which the active ingredient is distributed rapidly throughout the host body may be used, where the more dilute solutions are administered by infusion, but a depot or slow-release formulation may also be used. Particularly convenient sterile injectable compositions are sterile injectable solutions in isotonic saline or isotonic dextrose, buffered if necessary to a pH in a range of 5 to 9.

The sterile injectable compositions referred to above may be prepared as such and stored, but alternatively, the actual composition to be administered may be prepared immediately before it is to be used by adding a sterile medium to the sterile active ingredient, optionally containing another pharmaceutically acceptable diluent, which has been previously prepared and stored under sterile conditions.

The compositions of this invention may also be administered in the form of suppositories for rectal administration of the drug. These compositions can be prepared by mixing the drug with a suitable non-irritating excipient which is solid at ordinary temperatures but liquid at rectal temperature and will therefore melt in the rectum to release the drug. Such materials are cocoa butter and polyethyleneglycols.

The method of treatment of a human or animal subject for combatting renal disease by therapy or prophylaxis of the invention includes therapy or prophylaxis of post-ischemic acute renal failure, therapy or prophylaxis of nephrotoxic acute renal failure arising from antibiotic usage, therapy or prophylaxis of nephrotoxic acute renal failure arising from aminoglycosides, therapy or prophylaxis of nephrotoxic acute renal failure arising from amphotericin B, therapy or prophylaxis of nephrotoxic acute renal failure arising from metal usage or exposure, therapy or prophylaxis of nephrotoxic acute renal failure arising from mercuric chloride, therapy or prophylaxis of nephrotoxic acute renal failure arising from organic solvents, therapy or prophylaxis of nephrotoxic acute renal failure arising from carbon tetrachloride, therapy or prophylaxis of nephrotoxic acute renal failure arising from radiocontrast or other imaging agents, therapy or prophylaxis of nephrotoxic acute renal failure arising from myoglobinuric rhabdomyolysis, therapy or prophylaxis of nephrotoxic acute renal failure arising from hemoglobinuria and blood transfusion reactions, therapy or prophylaxis of nephrotoxic acute renal failure arising from myeloma light chains, therapy or prophylaxis of nephrotoxic acute renal failure arising from chemotherapeutic agents, therapy or prophylaxis of nephrotoxic acute renal failure arising from cis-platin, therapy or prophylaxis of nephrotoxic acute renal failure arising from any drug or pharmacologic agent, therapy or prophylaxis of acute renal failure arising from atheroembolic disease, therapy or prophylaxis of acute renal failure arising from renal artery occlusion, therapy or prophylaxis of acute renal failure arising from vasculitis, therapy or prophylaxis of acute renal failure arising from hemolytic-uremic syndrome, therapy or prophylaxis of acute renal failure arising from thrombolytic thrombocytopenic purpura, therapy or prophylaxis of acute renal failure arising from post-partum complications, therapy or prophylaxis of acute renal failure arising from Wegener's granulomatosis, therapy or prophylaxis of acute renal failure arising from polyarteritis, therapy or prophylaxis of acute renal failure arising from systemic lupus erythematosus, therapy or prophylaxis of acute renal failure arising from Henoch-Schoenlein purpura, therapy or prophylaxis of acute renal failure arising from anti-glomerular basement membrane disease, therapy or prophylaxis of acute renal failure arising from Goodpasture's syndrome, therapy or prophylaxis of acute renal failure arising from idiopathic rapidly progressive glomerulonephritis, therapy or prophylaxis of acute renal failure arising from acute glomerulonephritis, therapy or prophylaxis of acute renal failure arising from acute hypersensitivity interstitial nephritis, therapy or prophylaxis of acute renal failure arising from hypercalcemia, therapy or prophylaxis of acute renal failure arising from urinary tract obstruction, therapy or prophylaxis of acute renal failure arising from acute uric acid nephropathy, therapy or prophylaxis of acute renal failure arising from crystal deposition disease, therapy or prophylaxis of acute renal failure arising from pyelonephritis, therapy or prophylaxis of acute renal failure arising from papillary necrosis, therapy or prophylaxis of acute renal failure arising from hepatorenal syndrome, therapy or prophylaxis of acute renal failure arising from severe volume depletion, therapy or prophylaxis of acute renal failure arising from hypertension, therapy or prophylaxis of acute renal failure arising from burns, and therapy or prophylaxis of acute renal failure arising from bacterial sepsis.

Having generally described this invention, a further understanding will be obtained by reference to certain specific examples which are provided herein for purposes of illustration only and are not intended to be limiting unless otherwise specified.

EXAMPLES

Example 1

The effect of a test compound in accelerating renal repair was measured as follows:

Male Sprague-Dawley rats (250–325 g) were administered $HgCl_2$ (5 mg/kg sc) followed at 2 or 4 h with a single subcutaneous injection of EGF (20 μg) or placebo (0.9% NaCl). At time intervals of 24, 30, 48, and 72 hours after toxin administration, [$^3H$] thymidine incorporation into renal cortex, as well as blood urea nitrogen (BUN) and serum creatinine levels, were determined with methods known and practiced in the art. To obtain a complete time course for the BUN and serum creatinine levels, some animals were allowed to recover for as long as 12 days after $HgCl_2$ administration, and blood samples were obtained daily for BUN and serum creatinine levels.

This study produced a model of reversible nephrotoxic acute renal failure, as demonstrated in FIG. 1. Renal excretory function declined quickly following $HgCl_2$ injection, as reflected by BUN levels rising in the first 24 h from an average ($\pm$SE) control level of $21\pm2$ to a mean of $96\pm4$ mg/dl (n=32). BUN levels peaked to levels of $359\pm40$ mg/dl (n=7) at day 5 after toxic insult followed by progressive improvement thereafter to near normal levels by day 12.

As an indication of increases in cell regeneration, [$^3H$] thymidine incorporation into DNA of the kidney began to rise as early as 24 h with dramatic increases between 24 and 48 h after toxic injury (Table 1).

TABLE 1

| Effect of EGF on renal thymidine incorporation after $HgCl_2$ | | | | |
|---|---|---|---|---|
| [$^3H$] Thymidine Incorporation, dpm $\times$ $10^4$/mg DNA | | | | |
| 0 h | 24 h | 30 h | 48 h | 72 h |
| $HgCl_2$ 0.13 $\pm$ 0.04 | 8.42 $\pm$ 1.08 | 20.37 $\pm$ 4.24 | 64.16 $\pm$ 7.59 | 99.80 $\pm$ 28.04 |
| $HgCl_2$ + EGF 0.12 $\pm$ 0.03 | 13.81 $\pm$ 1.28 | 42.03 $\pm$ 5.45 | 80.52 $\pm$ 19.52 | 116.24 $\pm$ 13.80 |

Values are means $\pm$ SE; n = 4–8 animals for each group. Time course for renal thymidine incorporation in rats administered 5 mg/kg $HgCl_2$. Epidermal growth factor (EGF) was administered 2–4 h after nephrotoxin administration.

Histoautoradiographic studies were performed to determine the type of cells labeled with [$^3H$] thymidine after $HgCl_2$ exposure. Kidney sections from rats at 48 or 72 h after toxic administration were used for histoautoradiographic analysis. Labeling was confined to the nuclei. On average, 97.9% of the labeled cells were tubule cells, and 2.1% of the labeled cells were interstitial cells in the 60 examined fields. In control rats undergoing sham injection, 98.4% of labeled cells were tubule, and 1.6% were interstitial in 90 examined fields.

A single dose of exogenously administered EGF at 2 or 4 h after $HgCl_2$ resulted in higher rates of renal thymidine incorporation compared with values observed in non-EGF-treated animals receiving the nephrotoxin at 24, 30, 48, and 72 h (Table 1). When the EGF treatment group was compared with the nontreated group, the effect of EGF to increase renal thymidine incorporation was highly significant. Thus EGF significantly enhanced renal thymidine incorporation during the period of peak replicative and repair response of renal tubule cells to $HgCl_2$-induced cell necrosis. Of note, EGF treatment of control rats not receiving $HgCl_2$ did not demonstrate any increase in [$^3H$] thymidine incorporation in kidneys. At 24 h and after a single dose of EGF in rats undergoing sham $HgCl_2$ injection, renal [$^3H$] thymidine incorporation averaged $13\pm4\times10^3$ disintegrations per minute (dpm)/mg DNA, compared with a value of $12\pm2\times10^3$ dpm/mg DNA in non-EGF-treated sham animals (P=NS, n=4). Histoautoradiographic studies were performed to determine the location of the cells labeled with [$^3H$] thymidine in kidney sections from rats treated with EGF at 48 h after $HgCl_2$ injection. Labeling was again confined to nuclei. On average, 96.3% of labeled cells were identified as tubule, and 3.7% labeled cells were identified as interstitial cells in 60 fields.

To test the effect of EGF on renal tubule cell replication after $HgCl_2$-induced injury in a more absolute manner than measurement of the specific activity of renal [$^3H$] thymidine (Table 1), the number of labeled cells in renal cortex and outer medulla was determined at 24 and 48 h after $HgCl_2$ administration in both treatment groups. At 24 h EGF treatment increased the number of tubule cells incorporating [$^3H$] thymidine, as assessed by histoautoradiography, from $1.6\pm0.4$ in the nontreated groups to $7.5\pm1.8$ labeled cells/field in the treated group (P<0.02, n=3 rats and 60 fields for each group). Similarly at 48 h, EGF increased labeled tubule cells from a nontreated value of $12.1\pm1.8$ to $20.9\pm2.1$ cells/field (P21 0.01, n=3 rats and 60 fields for each group). Thus, EGF significantly enhanced renal tubule cell replication in the early reparative phase after nephrotoxic injury as assessed both by specific activity of [$^3H$] thymidine in the kidney and by absolute numbers of renal tubule cells incorporating labeled thymidine into DNA.

Figure 2:
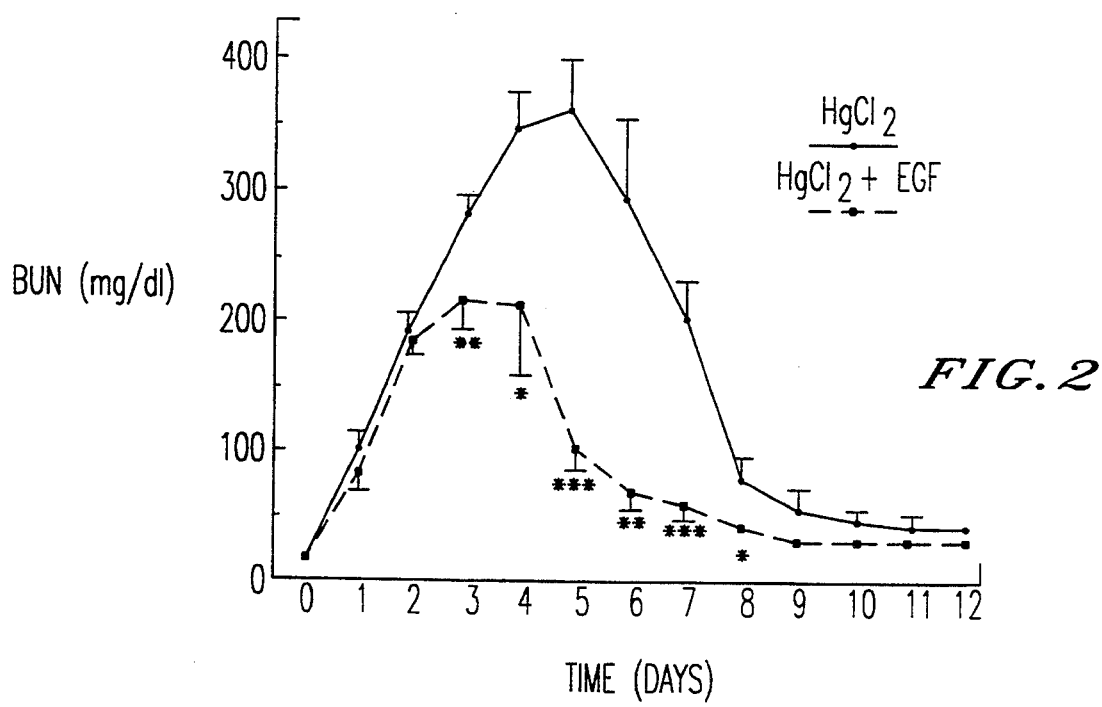

Associated with this EGF-induced enhancement of tubule cell thymidine incorporation, the time course of renal excretory failure after nephrotoxic injury, as measured by both BUN and serum creatinine levels, was dramatically altered by EGF treatment as demonstrated in FIGS. 1 and 2. EGF-treated animals had significantly lower peak BUN and serum creatinine levels, averaging $213\pm23$ and $6.54\pm0.72$ mg/dl, respectively, at 3 days after $HgCl_2$ injection, compared with peak levels of $359\pm40$ and $9.92\pm1.67$ mg/dl (P<0.001, n=7-16) at 5 days in nontreated nephrotoxic rats. EGF treatment also was associated with a return to near normal BUN and serum creatinine levels in EGF-treated animals on day 8, 4 days earlier than that observed in non-EGF-treated animals.

EGF treatment did not alter the degree of $Hg^{2+}$ presented to the kidney, because no difference in histological score of tubule cell injury was demonstrated between the nephrotoxic rats treated or not treated with EGF. Histological grading was assessed at 24 h, a time at which the peak of $HgCl_2$-induced toxic renal injury occurs and just before the accelerated regeneration repair phase. At 24 h, the mean histological scores in the inner cortex and outer stripe were $2.92\pm0.13$ and $4.70\pm0.07$, respectively, in the nephrotoxic non-EGF-treated rats vs. scores of $3.25\pm0.18$ and $4.65\pm0.08$, respectively, in the nephrotoxic EGF-treated rats (n=120 fields from 3 animals in each treatment group, P=NS for both scores). At 24 h after $HgCl_2$, extensive necrosis was present in proximal tubule segments with no difference in the degree of tubule cell necrosis observed histologically between the EGF-treated and nontreated groups receiving $HgCl_2$.

The results of the present experiments demonstrate that renal tubule cell repair and regeneration, as reflected by incorporation of radiolabeled thymidine within the kidney, begins as early as 24 h and accelerates between 24 to 48 h after $HgCl_2$ administration. As demonstrated by histoautoradiography, this renal thymidine incorporation into DNA was essentially confined to tubule cells.

The data presented in these studies demonstrate that exogenously administered EGF can play an important role in the repair and recovery from renal injury after a substantial nephrotoxic event. Exogenous EGF produced an accelerated renal tubule epithelial cell regenerative and repair response compared with normal response times after toxic renal tubule cell injury. This enhanced replicative and repair process led to a shortened time to recover renal excretory function compared with time required in nontreated animals.

Example 2

Sprague Dawley rats (250–325 g) were anesthetized with a short-acting barbiturate, the abdominal cavity was exposed, and both left and right renal arteries were identified and clamped for 30 minutes. The clamps were released and perfusion to the kidneys reestablished. At time intervals of 24, 48, and 72 hours after ischemia and reperfusion, $^3$H-thymidine incorporation into kidneys, as well as blood urea nitrogen (BUN) and serum creatinine levels. To obtain a complete time course, some animals were allowed to recover for 7 days after renal ischemia and blood samples were then obtained daily for BUN or serum creatinine measurements.

To localize and identify the cells incorporating the radiolabeled thymidine within the kidney, histoautoradiography of kidney samples was also accomplished. For quantitative evaluation, a computerized operator-interactive system was used. Sections were examined at 276 magnification, and 10–15 fields were counted in the cortex and outer and inner stripes of the outer medulla in each section for an individual animal. The cell type of the labeled cells was identified as either tubular or interstitial.

For the experiments that used EGF, rats were administered EGF (20 μg) subcutaneously 1–1.5 hours after surgery. This dose of EGF is substantially lower than those employed in previously reported studies that administered EGF systemically. At varying time points after reperfusion, measurements of $^3$H-thymidine incorporation into the kidneys and BUN, and serum creatinine levels were determined. Some animals receiving EGF were allowed to recover for up to 7 days with serial determinations of BUN and serum creatinine.

The experimental design of this study produced a model of reversible ischemic acute renal failure. Renal excretory function declined quickly after 30 minutes of bilateral renal artery clamping as reflected by BUN levels rising in the first 24 hours of reperfusion from an average (±SE) control level of 21±2 to a mean of 126±9 mg/dl (n=12). BUN levels peaked to levels of 158±21 (n=13) at 48 h after ischemic insult and progressively improved thereafter, returning to near normal levels by day 7 (168 h).

As an indication of an increase in cell regeneration, $^3$H-thymidine incorporation into DNA of the kidney began to rise between 24 to 48 hours after renal ischemia, demonstrating at least a 24 hour delay compared with the rise in BUN levels. Peak $^3$H-thymidine incorporation, averaging $255 \pm 78 \times 10^3$ dpm/mg DNA, occurred at 72 hours and fell precipitously thereafter.

Histoautoradiographic studies were performed to determine the location of the cells labeled with $^3$H-thymidine. Kidney sections from rats at 48 hours after renal ischemia were used for histoautoradiographic analysis. Labeling was confined to the nuclei. On average, 97.8% of the labeled cells were tubule cells (absolute number=3,350 cells) and 2.2% of the labeled cells were interstitial cells (absolute number=73 cells) in 90 fields evaluated. In control rats undergoing sham renal ischemia, 98.7% of labeled cells were tubule (absolute number=230) and 1.3% were interstitial (absolute number=3) in 90 examined fields. The distribution of labeled tubule cells in postischemic kidneys at 48 hours demonstrated that 52, 33, and 15% of all labeled tubule cells were located in cortex and outer and inner stripes of the outer medulla, respectively.

A single dose of exogenously administered EGF at 1–1.5 hours after reperfusion significantly increased renal thymidine incorporation compared with control nontreated ischemia values measured at 24, 48, 72 hours of reperfusion after 30 minutes of bilateral renal artery clamping. Thus, EGF both accelerated and enhanced renal thymidine incorporation at all time periods through the peak replicative and repair response of renal tubule cells compared with values of the nontreated ischemia group. EGF treatment of rats undergoing sham ischemia did not show any increase in $^3$H-thymidine incorporation average $14 \pm 5$ $10^3$ dpm/mg DNA in non-EGF treated sham animals (P=NS, n=3).

Histoautoradiographic studies were performed to determine the location of the cells labeled with $^3$H-thymidine in kidney sections from rats treated with EGF at 24 hours. Labeling was once again almost exclusively in tubule cells with, on average, 98.1% of labeled cells identified as tubule (absolute number=3,183) and 1.9% labeled cells (absolute number=61) identified as interstitial cells. The distribution of labeled tubule cells in postischemic kidneys at 24 hours after EGF administration demonstrated that 27, 68, and 5% of labeled cells were found in cortex and outer and inner stripes of the outer medulla, respectively. This distribution demonstrates a modest shift towards earlier repair in the outer stripe after EGF treatment compared with untreated ischemic kidneys.

Figure 3:
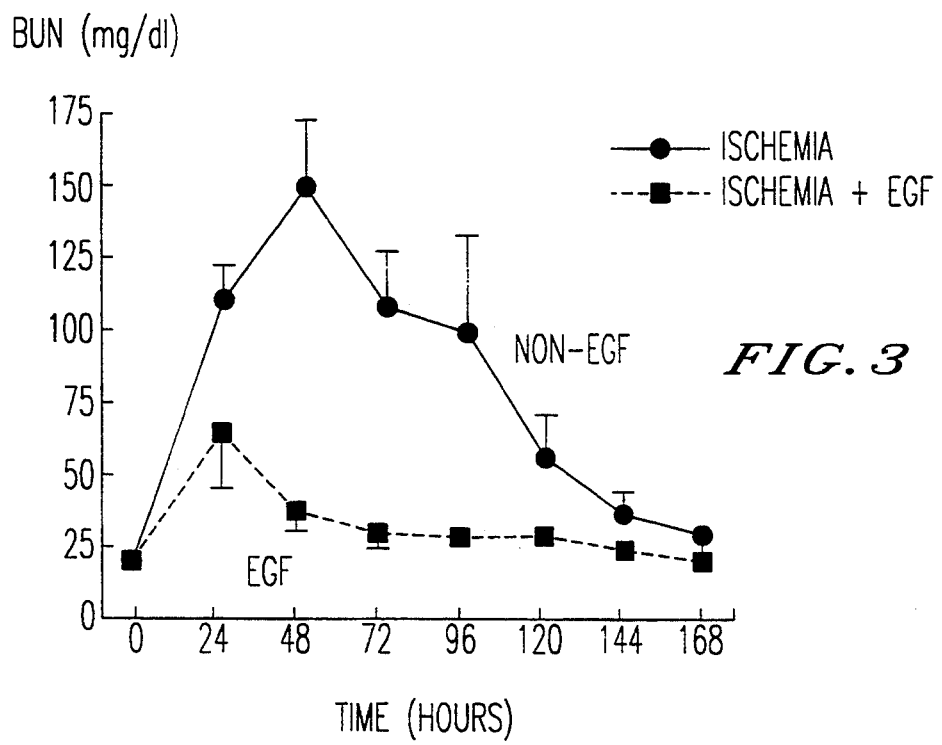
Figure 4:
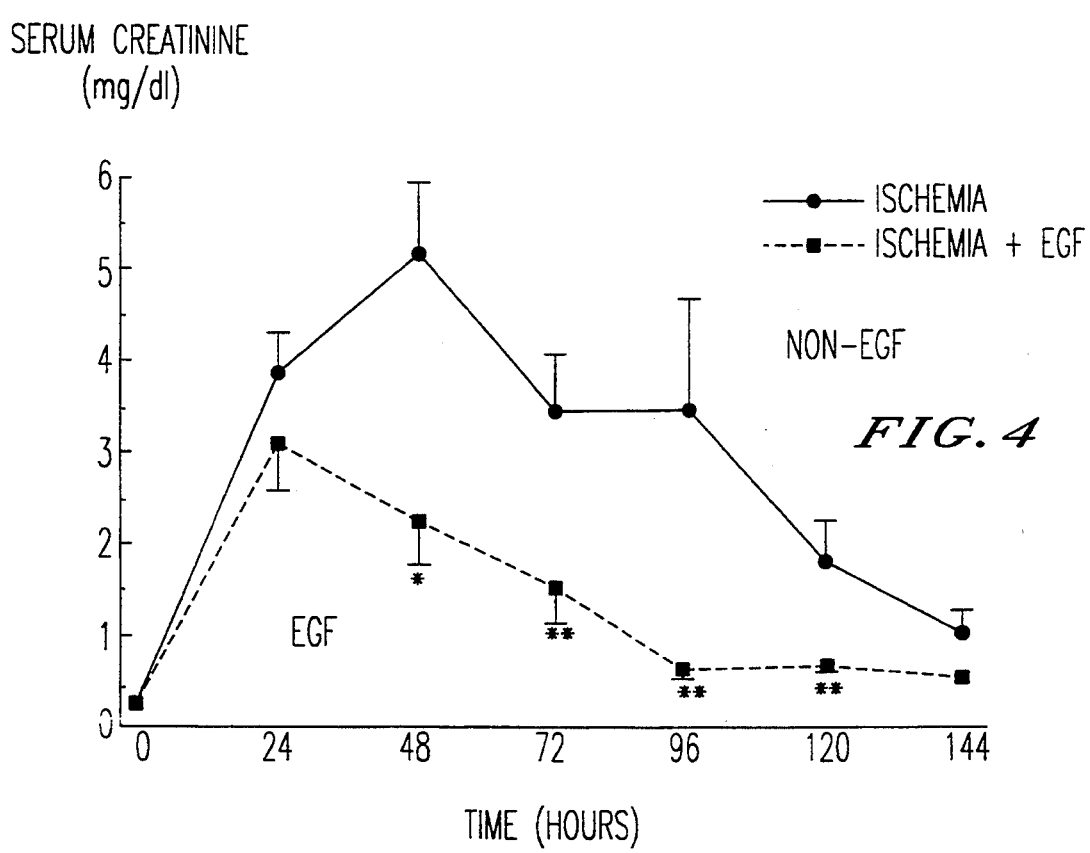

Associated with this EGF-induced enhancement of tubule cell thymidine incorporation, the time course of renal excretory failure, as measured by both BUN and serum creatinine levels after ischemic injury, was dramatically altered by EGF treatment as demonstrated in FIGS. 3 and 4. A group of animals were treated with a single dose of EGF within 1–1.5 hours of reperfusion after 30 minutes of bilateral renal ischemia and followed for 3–7 days. The BUN and creatinine levels of EGF-treated animals, were significantly lower during the entire 7-day period of acute renal failure, demonstrating an EGF-mediated enhancement in renal function recovery after ischemia.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of treating a human or animal subject with renal failure by therapy or prophylaxis, comprising subcutaneously injecting into said subject a composition comprising (i) an amount, effective for said treatment, of transforming growth factor-α (TGF-α) or TGF-α and epidermal growth factor (EGF) and (ii) a sterile, non-toxic, pharmaceutically acceptable diluent or solvent.

2. The method of claim 1, comprising administering to said subject epidermal growth factor (EGF) and transforming growth factor-α (TGF-α), a physiologically acceptable salt thereof, a solvate thereof, a complex thereof, or a mixture of these.

3. The method of claim 2, comprising administering said epidermal growth factor to said subject in an amount sufficient to obtain from 1 ng $kg^{-1}$ body weight to 10 mg $kg^{-1}$ body weight of said epidermal growth factor.

4. The method of claim 2, comprising administering to said subject from 10 ng $kg^{-1}$ body weight to 1 mg $kg^{-1}$ body weight of said epidermal growth factor.

5. The method of claim 2, wherein said subject is a human.

6. The method of claim 1, comprising administering to said subject transforming growth factor-α (TGF-α), a physiologically acceptable salt thereof, a solvate thereof, a complex thereof, or a mixture of these.

7. The method of claim 6, comprising administering said transforming growth factor-α in an amount of from 1 ng $kg^{-1}$ body weight to 10 mg $kg^{-1}$ body weight of said transforming growth factor-α.

8. The method of claim 6, comprising administering to said subject from 10 ng $kg^{-1}$ body weight to 1 mg $kg^{-1}$ body weight of said transforming growth factor-α.

9. The method of claim 6, wherein said subject is a human.

10. The method of claim 1, wherein said renal failure is a renal disease.

11. The method of claim 2, comprising administering said transforming growth factor-α to said subject in an amount sufficient to obtain from 1 ng $kg^{-1}$ body weight to 10 mg $kg^{-1}$ body weight of said transforming growth factor-α.

12. The method of claim 2, comprising administering to said subject from 10 ng $kg^{-1}$ body weight to 1 mg $kg^{-1}$ body weight of said transforming growth factor-α.

* * * * *

UNITED STATES PATENT AND TRADEMARK OFFICE
CERTIFICATE OF CORRECTION

PATENT NO. : 5,360,790

DATED : NOVEMBER 1, 1994

INVENTOR(S) : H. DAVID HUMES

It is certified that error appears in the above-identified patent and that said Letters Patent is hereby corrected as shown below:

Column 8: line 33, "P21 0.01,"
should read --P< 0.01,--

Signed and Sealed this

Fifteenth Day of August, 1995

Attest:

BRUCE LEHMAN

Attesting Officer      Commissioner of Patents and Trademarks